(12) United States Patent
Koehler et al.

(10) Patent No.: US 9,044,187 B2
(45) Date of Patent: Jun. 2, 2015

(54) POST-PATIENT DYNAMIC FILTER FOR COMPUTED TOMOGRAPHY (CT)

(75) Inventors: Thomas Koehler, Norderstedt (DE); Holger Schmitt, Hamburg (DE); Roland Proksa, Neu Wulmstorf (DE)

(73) Assignee: Koninklijke Philips N.V., Eindhoven (NL)

( * ) Notice: Subject to any disclaimer, the term of this patent is extended or adjusted under 35 U.S.C. 154(b) by 159 days.

(21) Appl. No.: 13/992,302

(22) PCT Filed: Dec. 2, 2011

(86) PCT No.: PCT/IB2011/055435
§ 371 (c)(1),
(2), (4) Date: Jun. 7, 2013

(87) PCT Pub. No.: WO2012/077027
PCT Pub. Date: Jun. 14, 2012

(65) Prior Publication Data
US 2013/0259191 A1    Oct. 3, 2013

Related U.S. Application Data

(60) Provisional application No. 61/421,324, filed on Dec. 9, 2010.

(51) Int. Cl.
*A61B 6/00* (2006.01)
*A61B 6/03* (2006.01)
(Continued)

(52) U.S. Cl.
CPC .............. *A61B 6/4035* (2013.01); *A61B 6/032* (2013.01); *A61B 6/488* (2013.01); *G21K 1/10* (2013.01); *A61B 6/06* (2013.01); *A61B 6/4241* (2013.01); *A61B 6/4291* (2013.01); *A61B 6/544* (2013.01)

(58) Field of Classification Search
CPC ...... A61B 6/4035; A61B 6/032; A61B 6/488; A61B 6/06; A61B 6/4241; A61B 6/4291; A61B 6/544; G21K 1/10
USPC ................................ 378/4, 19, 98.8, 156–159
See application file for complete search history.

(56) References Cited

U.S. PATENT DOCUMENTS 3,755,672 A * 8/1973 Edholm et al. ................ 378/158
4,963,746 A   10/1990 Morgan et al.
(Continued)

FOREIGN PATENT DOCUMENTS

JP    2008173233 A    7/2008
WO   2009063353 A2   5/2009
(Continued)

*Primary Examiner* — Irakli Kiknadze

(57) ABSTRACT

An imaging system includes a radiation source (310) configured to rotate around an examination region about a z-axis and having a focal spot that emits a radiation beam that traverses the examination region. The system further includes a radiation sensitive detector array (314) with a plurality of detector pixels that detects radiation traversing the examination region and generates projection data indicative of the detected radiation. The system further includes a dynamic post-patient filter (316) including one or more filter segments (402, 802, 902, 1004, 1102). The filter is configured to selectively and dynamically move in front of the detector array between the detector array and the examination region and into and out of a path of the radiation beam illuminating the detector pixels during scanning an object or subject based on a shape of the object or subject, thereby filtering unattenuated radiation and radiation traversing a periphery of the object or subject.

24 Claims, 7 Drawing Sheets

(51) Int. Cl.
*G21K 1/10* (2006.01)
*A61B 6/06* (2006.01)

(56) References Cited

U.S. PATENT DOCUMENTS

| | | | |
|---|---|---|---|
| 4,972,458 A * | 11/1990 | Plewes | 378/146 |
| 5,552,606 A | 9/1996 | Jones et al. | |
| 6,108,403 A | 8/2000 | Cooper, III et al. | |
| 6,501,828 B1 * | 12/2002 | Popescu | 378/150 |
| 7,200,201 B2 | 4/2007 | Unger et al. | |
| 7,272,208 B2 * | 9/2007 | Yatsenko et al. | 378/145 |
| 7,313,224 B1 * | 12/2007 | Saunders et al. | 378/108 |
| 7,649,981 B2 | 1/2010 | Seppi et al. | |
| 2005/0201512 A1 | 9/2005 | Mueller | |
| 2007/0104320 A1 | 5/2007 | Arenson et al. | |

FOREIGN PATENT DOCUMENTS

| | | |
|---|---|---|
| WO | 2009136400 A2 | 11/2009 |
| WO | 2010133920 A1 | 11/2010 |

* cited by examiner

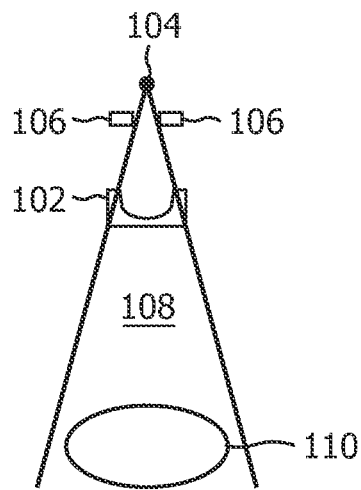
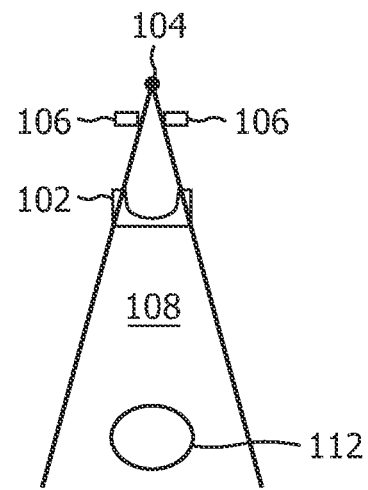
FIG. 1A          FIG. 1B
(PRIOR ART)
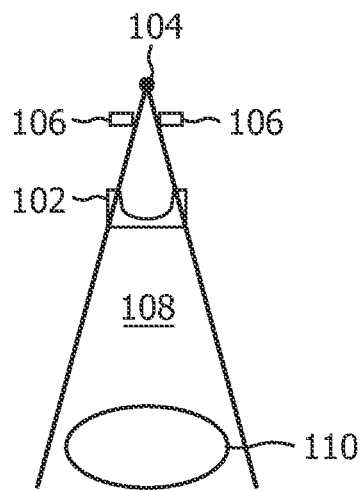
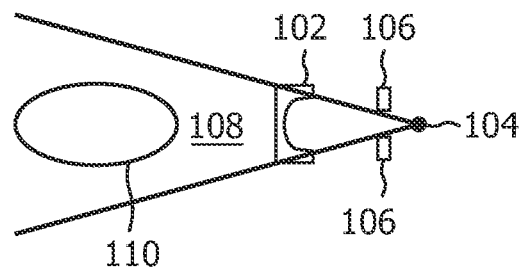
FIG. 2A          FIG. 2B
(PRIOR ART)

POST-PATIENT DYNAMIC FILTER FOR COMPUTED TOMOGRAPHY (CT)

The following generally relates to imaging and more particularly to a post-patient filter utilized to reduce x-ray flux at the periphery or edges of the radiation beam in computer tomography (CT) scanners.

A conventional CT scanner includes an x-ray tube that emits radiation. A source collimator is disposed between the x-ray tube and an examination region and collimates the emitted radiation to produce a fan or cone shaped x-ray beam. The collimated beam traverses the examination region and an object or subject therein (which attenuates the beam as a function of the radiodensity of the object or subject) and illuminates a detector array disposed across the examination region from the x-ray tube. The detector produces projection data indicative of the detected radiation, and the projection data has been reconstructed to generate volumetric image data indicative of the object or subject.

A so-called bowtie filter (note that the name of this filter generally reflects the typical physical shape of the filter) has been positioned between the source collimator and the examination region and attenuates the fan or cone shape x-ray beam to a greater degree at the outer regions or peripheral rays of the beam, thereby reducing the flux at the outer regions of the fan or cone beam. Such filtering is well-suited for photon counting detectors, which suffer from insufficient count rate capabilities. By way of example, in a typical CT scan, excessive count rates are only required for rays of the beam that do not cross the subject (i.e., rays that are not attenuated) or that travel only short distances through the subject in peripheral regions (i.e., rays that are attenuated by less than a predetermined amount). Such filtering is also well-suited to be employed with scanners with non-counting detectors, for example, which can improve radiation efficiency, etc.

FIGS. 1 and 2 illustrate an example of a conventional pre-patient bowtie filter 102 in connection with an x-ray source 104, a source collimator 106, and an examination region 108, and portions of subjects 110 and 112 being scanned. Theoretically, the bowtie filter 102 corresponds to the profile or shape of the subject being scanned, and heavily filters the regions of the beam that traverse only air, lightly filters the region of the beam that traverses the subject, and smoothly transitions the degree of filtering for transitions there between so that a correct x-ray profile can be achieved. An air scan is performed to measure the attenuation profile of the filter and to generate a calibration based thereon for detector pixel normalization during reconstruction.

Unfortunately, the profile of every subject is not the same as the shape of the subject may be larger for some subjects, smaller for other subjects, and may also be different such as more or less cylindrical as shown in FIGS. 1(A) and 1(B). Furthermore, the profile of the same subject may be quite different depending on the angle at which the subject is viewed as shown in FIGS. 2(A) and 2(B). As a consequence, the bowtie filter 102 may be better-suited for some subjects but not be well-suited for other subjects, for example, the subjects 110 and 112, since the filter 102 does not match the profile of the subjects 110 and 112. In addition, a subject may be positioned off-center such that a portion of the beam traversing air is lightly filtered, and a portion of the beam traversing the subject is heavily filtered. As a result, photon flux at the edges of the subject may decrease the fidelity of the detector output to a level that may be prohibitively low for diagnostically valuable images.

Aspects of the present application address the above-referenced matters and others.

According to one aspect, an imaging system includes a radiation source configured to rotate around an examination region about a z-axis and has a focal spot that emits a radiation beam that traverses the examination region. The system further includes a radiation sensitive detector array with a plurality of detector pixels that detects radiation traversing the examination region and generates projection data indicative of the detected radiation. The system further includes a dynamic post-patient filter including one or more filter segments. The filter is configured to selectively and dynamically move in front of the detector array between the detector array and the examination region and into and out of a path of the radiation beam illuminating the detector pixels during scanning an object or subject based on a shape of the object or subject, thereby filtering unattenuated radiation and radiation traversing a periphery of the object or subject.

According to another aspect, a method includes filtering peripheral rays of an emitted radiation beam traversing an examination region with dynamically adjustable filter segments configured to selectively move in and out of a region in front of a detector array and between the detector array and an examination region during scanning of an object or subject based on a shape of the object or subject, thereby filtering unattenuated radiation and radiation traversing a periphery of the object or subject.

According to another aspect, a method for reducing a flux of peripheral rays of a radiation beam includes dynamically filtering the peripheral rays during scanning of a object or subject by selectively positioning physical filter segments of a dynamically adjustable post-patient filter between a detector array and an examination region of an imaging system based on a shape of the object or subject.

The invention may take form in various components and arrangements of components, and in various steps and arrangements of steps. The drawings are only for purposes of illustrating the preferred embodiments and are not to be construed as limiting the invention.

FIG. 1A illustrates a prior art bowtie filter in connection with a first patient, having a first shape, being scanned.

FIG. 1B illustrates the prior art bowtie filter of FIG. 1 in connection with a second patient, having a second shape, being scanned.

FIG. 2A illustrates a prior art bowtie filter positioned at a first angle in connection with a generally elliptical shaped patient being scanned.

FIG. 2A illustrates a prior art bowtie filter positioned at a second angle in connection with a generally elliptical shaped patient being scanned.

FIG. 3 illustrates an imaging system 300 such as a computed tomography (CT) scanner.

Figure 3:
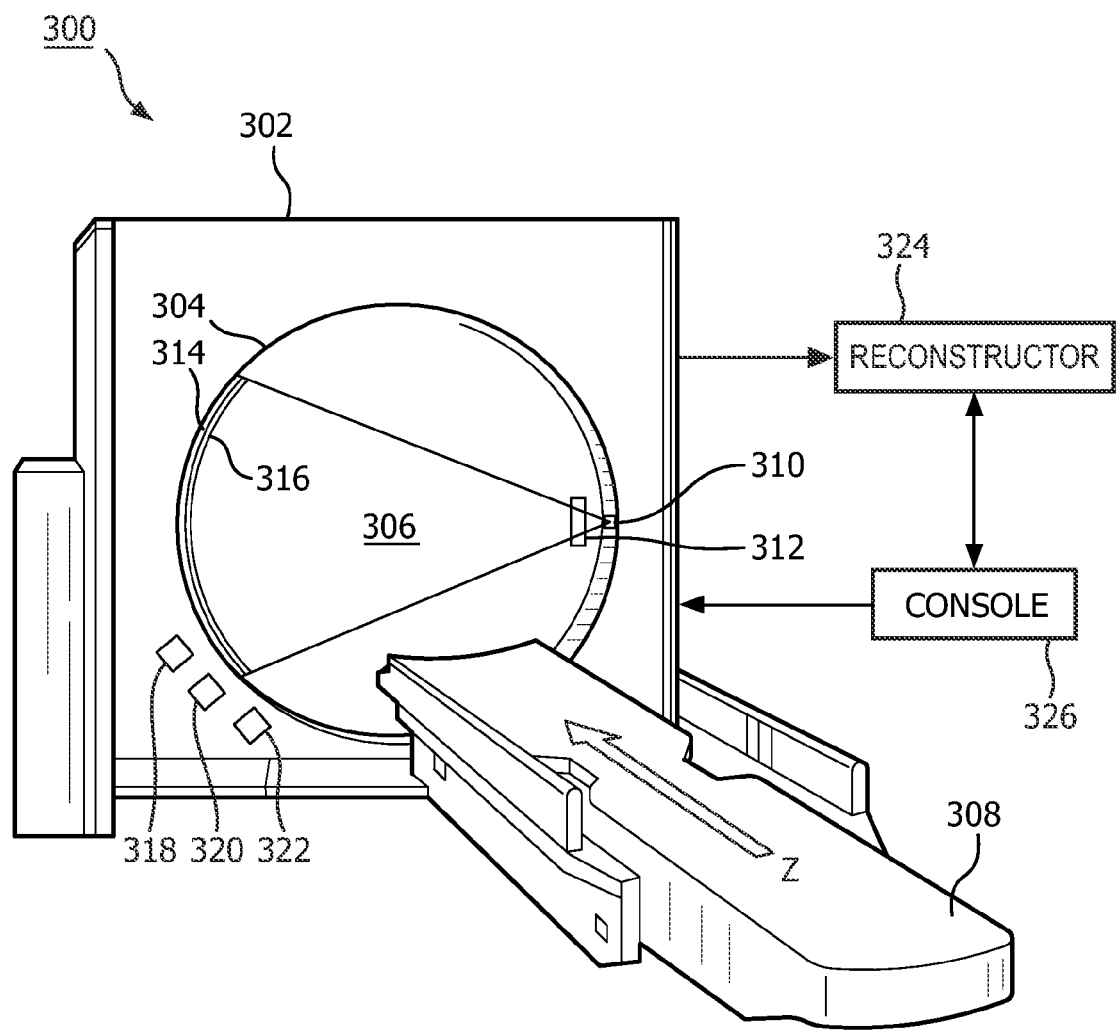
FIG. 3 illustrates an example imaging system including a dynamic post-patient filter for reducing x-ray flux at the periphery of the radiation beam.

The imaging system 300 includes a stationary gantry 302 and a rotating gantry 304, which is rotatably supported by the stationary gantry 302. The rotating gantry 304 rotates around an examination region 306 about a longitudinal or z-axis.

A support 308, such as a couch, supports a subject in the examination region 306 and can be used to position the subject with respect to x, y, and/or z axes before, during and/or after scanning.

A radiation source 310, such as an x-ray tube, is supported by the rotating gantry 304 and rotates with the rotating gantry 304 about the examination region 306, and emits radiation, via a focal spot, that traverses the examination region 306. A source collimator 312 collimates the emitted radiation, forming a generally fan, cone, or other shaped beam that traverses the examination region 306.

A radiation sensitive detector array 314 is located opposite the radiation source 310, across the examination region 306. The detector array 314 includes one or more rows, each including a plurality of detector pixels that detect radiation traversing the examination region 306 and generate projection data indicative of the detected radiation. The detector array 314 may include photon-counting, energy-resolving, and/or integrating detectors.

A post-patient dynamic filter 316 is configured for movement in and out of a region in front of the detector array, between the detector array 314 and the examination region 306 and in a path of the radiation beam, and filters the beam traversing the examination region 306. As described in greater detail below, the dynamic filter 316 is configured to dynamically (symmetrically or asymmetrically) adjust its physical profile, through movement of one or more sub-filters or filter segments thereof, based on the shape of the subject or object being scanned during scanning.

The dynamic adjustment allows the dynamic filter 316 to dynamically adjust based on the profile of each patient, which allows the dynamical filter 316 to be tuned to the profile of each patient. As such, the dynamic filter 316 can be used to filter and/or reduce the x-ray flux at the periphery of the radiation beam, for example, in connection with counting detectors and/or improve radiation efficiency in connection with integrating detectors. In addition, the filter can be asymmetrically adjusted, for example, where the subject is positioned off-center.

The movement of the one or more sub-filters or filter segments can be achieved through one or more motors 318 in mechanical communication with the one or more sub-filters or filter segments, one or more position sensors 320 (e.g., encoders) that sense motor position, and a controller 322 that controls the one or motors 318 to move, individually or in a pre-determined combination, the one or more filter sub-filters or filter segments along a predefined path such as a track, a rail, or the like. The dynamic filter 316 can be used in connection with and/or in place of a conventional pre-patient bowtie filter.

A reconstructor 324 reconstructs the processed projection data and generates volumetric image data indicative of the examination region 306. The resulting volumetric image data can be processed by an image processor or the like to generate one or more images.

A general purpose computing system serves as an operator console 326, and includes an output device such as a display and an input device such as a keyboard, mouse, and/or the like. Software resident on the console 326 allows the operator to control the operation of the system 300, for example, allowing the operator to select a protocol that employs the dynamic filter 316, initiate scanning, etc.

Figure 4:
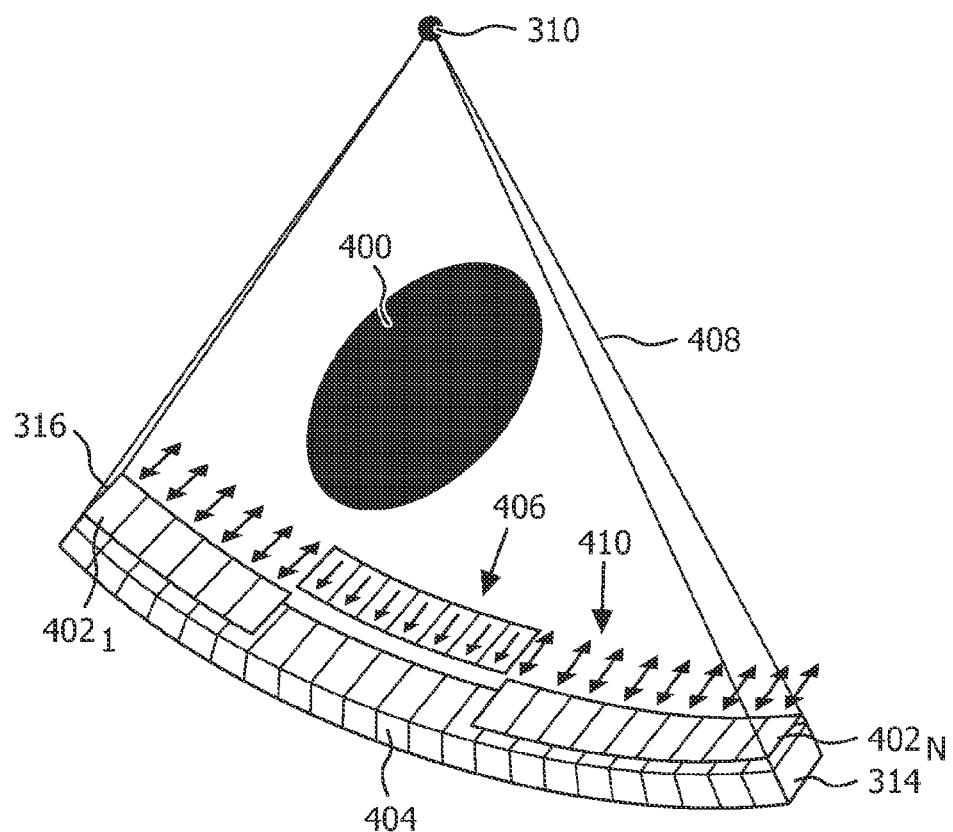
FIG. 4 illustrates an example dynamic post-patient filter in which the filter moves along the z-axis.

FIG. 4 illustrates a non-limiting example of the dynamic filter 316 in connection with the source 310, the detector array 314 and a subject 400 being scanned. In this example, the filter 316 includes N sub-filters (or filter segments) $402_1, \ldots, 402_N$ (where N is an integer equal to or greater than one), collectively referred to herein as sub-filters 402. As shown, each of the sub-filters 402 corresponds to a single and different detector pixel 404 of the detector array 314.

In this embodiment, the motor 318 includes a sub-motor for each of the sub-filters 402, and each sub-motor selectively and individually moves a single sub-filter 402 between a first position 406 at which the filter 402 is outside of a path of a radiation beam 408 illuminating the detector pixel 404 and a second position 410 at which the sub-filter 402 is in front of a detector pixel 404, thereby filtering the radiation illuminating the detector pixel 404.

In another instance, the motor 318 may include a single motor configured to independently drive each of the sub-filters 402. In yet another instance, the motor 318 may include multiple motors but less motors than the number of sub-filters 402, with one or more of the motors 318 configured to control more than one sub-filter 402. Other motor configurations are also contemplated herein.

In the illustrated embodiment, the motor 318 is configured to move the sub-filter 402 fast enough to cover and/or uncover a pixel within one data acquisition interval for each acquisition angle. By way of example, in one instance a filter can be moved between at a rate in a range of half a millimeter per millisecond to two millimeters per millisecond. Faster and slower rates are also contemplated herein.

Various approaches can be utilized to determine which sub-filters 402 cover detector pixels 404 during a given acquisition interval. For example, in one instance a pre-scan (e.g., scout, pilot, etc.) is performed and the resulting data is used for planning the scan, including identifying a perimeter of the object 400. In another instance, the perimeter of the object 400 is estimated during scanning based on relative intensity values of the detected data.

Where the subject 400 is centered in the examination region 306, the sub-filters 402 can be symmetrically controlled with respect of a center region of the detector array so that an equal number of sub-filters 402 of both sides of the center region are utilized. In instances in which the object 400 is positioned off-center, the sub-filters 402 can be asymmetrically controlled in which a different number of sub-filters 402 is used on both sides of the center region.

Figure 5:
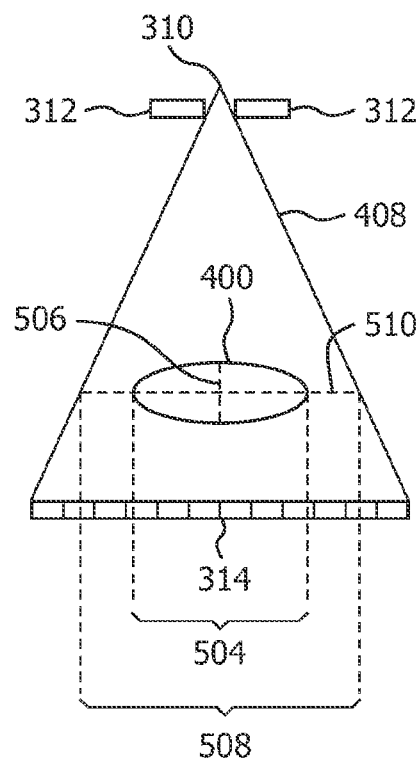
FIGS. 5, 6 and 7 illustrate an example of the dynamic filter dynamically moving in connection with an object and a rotating radiation source.
Figure 6:
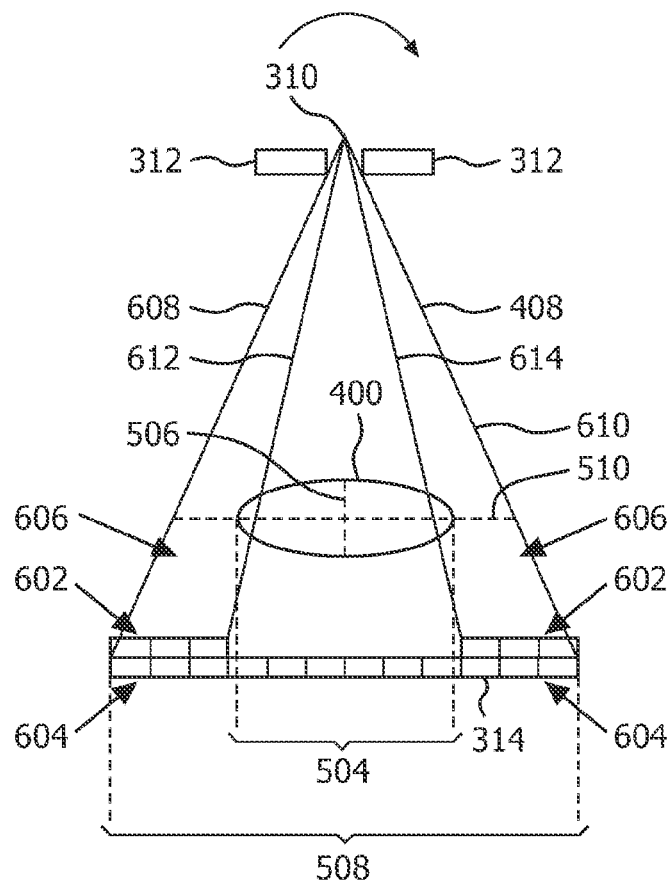
Figure 7:
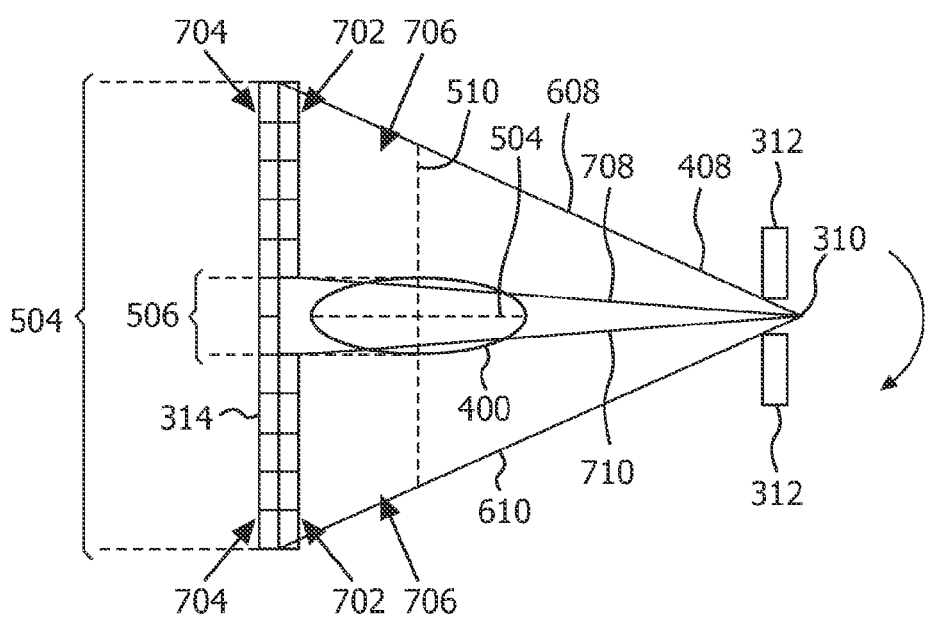

FIGS. 5, 6 and 7 illustrate an example of dynamically adjusting the sub-filters 402 in accordance with a generally elliptically shaped object 400 having a width 504 and a height 506. With this embodiment, the sub-filters 402 move in a direction of the z-axis and perpendicular to the direction of the beam 408.

Initially referring to FIG. 5, the beam 408 is collimated (via the collimator 312 or otherwise) such that a width 508 of the beam 408 at an image plane 510 is wider than the width 504 of the object 400, and the sub-filters 402 are positioned outside of the beam 408. This particular configuration is for explanatory purposes and is not limiting. For example, in another instance, the filter 316 may cover the entire or a sub-portion of the array 314.

In FIG. 6, the source 310 is moving through the twelve o'clock position. At this position, subsets 602 of the sub-filters 402 are moved over subsets 604 of the detector pixels of the detector array 314 in accordance with the width 504 of the object 400. With the sub-filters 402 as such, portions 606 of the radiation beam 408 between outer rays 608 and 610 and rays 612 and 614 traversing paths at the periphery (within and near the edges of a perimeter) of the object 400 along the width 508 are filtered by the subsets 602 of sub-filters 402 before illuminating the subsets 604 of the detector pixels.

In FIG. 7, the source 310 is moving through the three o'clock position. At this position, subsets 702 of the sub-filters 402 are moved over subsets 704 of the detector pixels of the detector array 314 in accordance with the height 506 the object 400. With the sub-filters 402 as such, portions 706 of the radiation beam 408 between the outer rays 608 and 610 and rays 708 and 710 traversing paths at the periphery (within and near the edges of a perimeter) of the object 400 along the height 506 of the object 400 are filtered by the subsets 702 of sub-filters 402 before illuminating the subsets 704 of the detector pixels.

With respect to FIGS. 5-7, note that the profile of the subject 400 and hence number of sub-filters 402 in the subsets 602 and 702 positioned over the detector array 314 are different at the twelve o'clock position (FIG. 6) and the three o'clock position (FIG. 7), with number of sub-filters 420 following the profiled of the subject 40. During scanning, the relative position of the moving sub-filters 402 can be tracked e.g., via an encoder or the like and/or estimated. Furthermore, the sub-filters 402 can be continuously or discretely (at predetermined uniform or non-uniform intervals) dynamically adjusted as the source 310 rotates through one or more viewing angles around the examination region 306.

Figure 8:
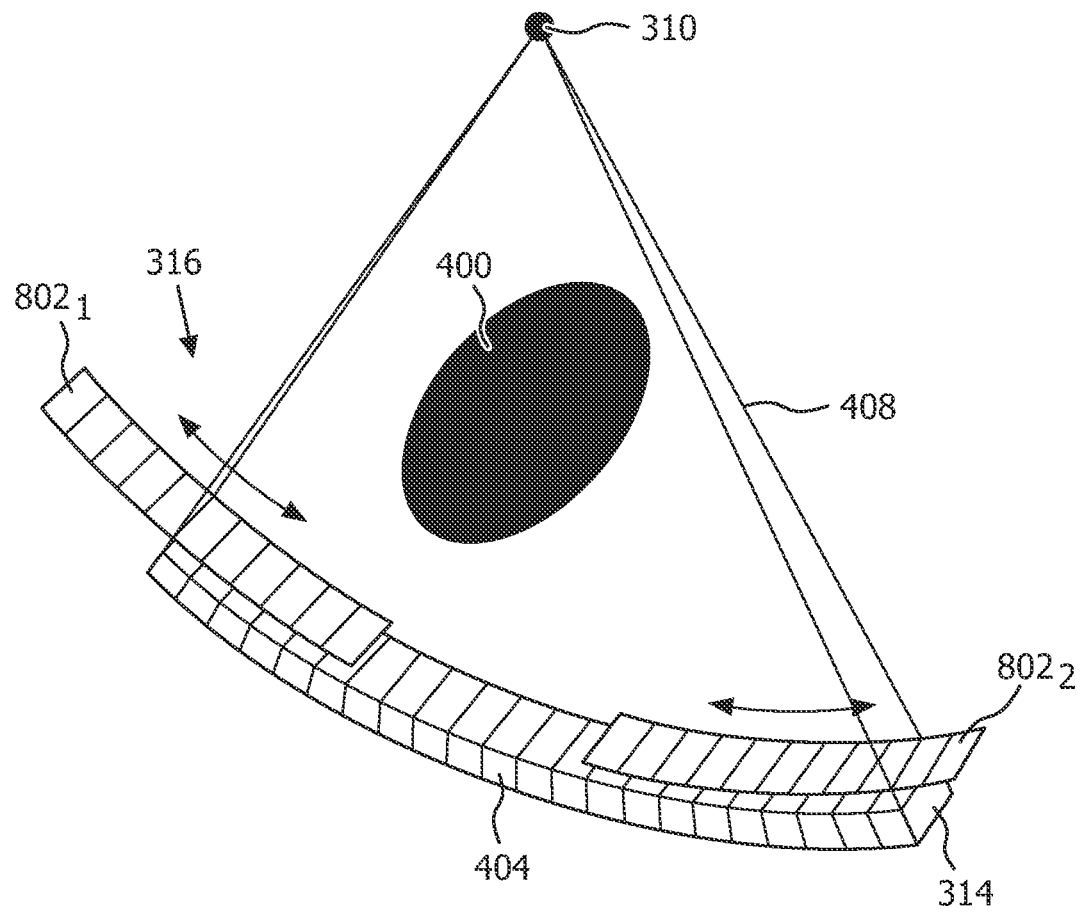
FIG. 8 illustrates an example dynamic post-patient filter in which the filter moves along a direction transverse to the z-axis.

FIG. 8 illustrates another non-limiting example of the filter 316. In this example, the filter 316 is split into two different filter segments 802₁ and 802₂, which move oppositely in a direction transverse to the z-axis, perpendicular to the direction of the beam 408, and along a (curve or linear) long axis of the detector array 314. Each filter segment may be controlled with the same or a different motor. Likewise, the filter segments 802₁ and 802₂ move in coordination with the perimeter of the subject 400 during scanning.

Figure 9:
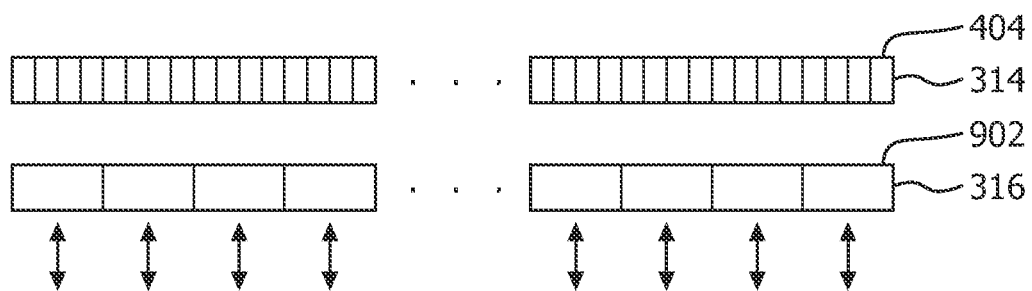
FIG. 9 illustrates an embodiment in which the dynamic post-patient filter includes a plurality of filter segments, each corresponding to more than one detector pixel.

FIG. 9 illustrates another non-limiting example of the filter 316. In this example, the filter 316 includes a single row of filter segments 902. Each of the filter segments 902 corresponds to a plurality (e.g., four (4) in the illustrated example) of the detector pixels 404. The motor 318 includes a motor for each of the filter segments 902, and each motor is configured to move a corresponding filter segment 902 over and in front of or away from a respective plurality of detector pixels.

Figure 10:
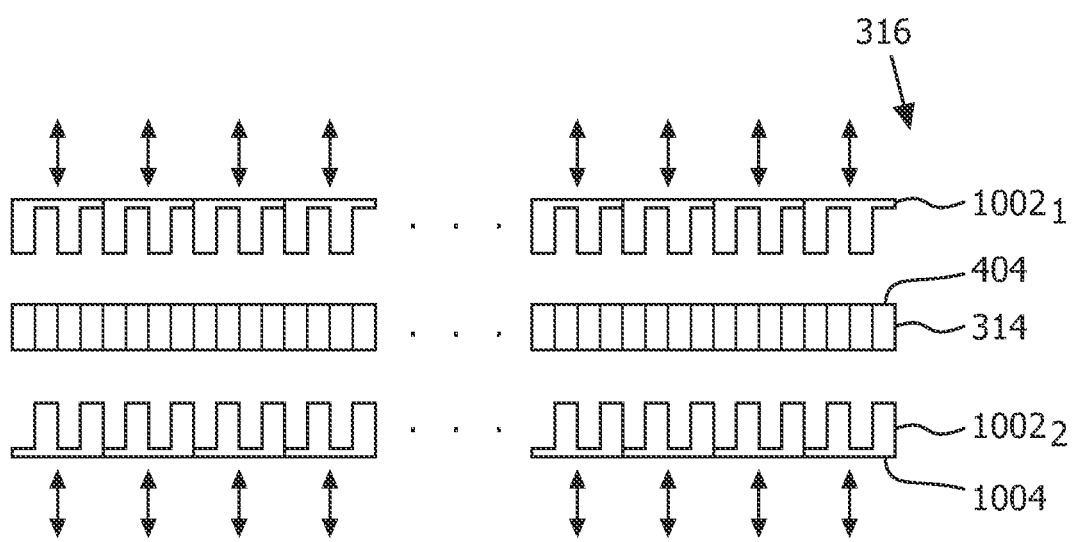
FIG. 10 illustrates an embodiment in which the dynamic post-patient filter includes two rows of interleaved detector filter comb segments.

FIG. 10 illustrates another example of the filter 316. In this example, the filter 316 is split into a two rows 1002₁ and 1002₂ of interleaved comb segments 1004 with each row located on opposite sides of the detector array 314 along the z-axis direction. In this example, the two rows 1002₁ and 1002₂ are alternately moved over detector pixels so that only one of the rows covers a corresponding set (e.g., four (4) in the illustrated example) of detector pixels 404 at any given time. As such, only every other group of detector pixels 404 can be unusable in that it may include detector pixels be only partially covered by the row for a given acquisition interval. Where a pixel is only partially covered by a filter, the reading can be discarded, and a new reading derived by interpolating the two adjacent detector readings from unfiltered detector pixels.

Figure 11:
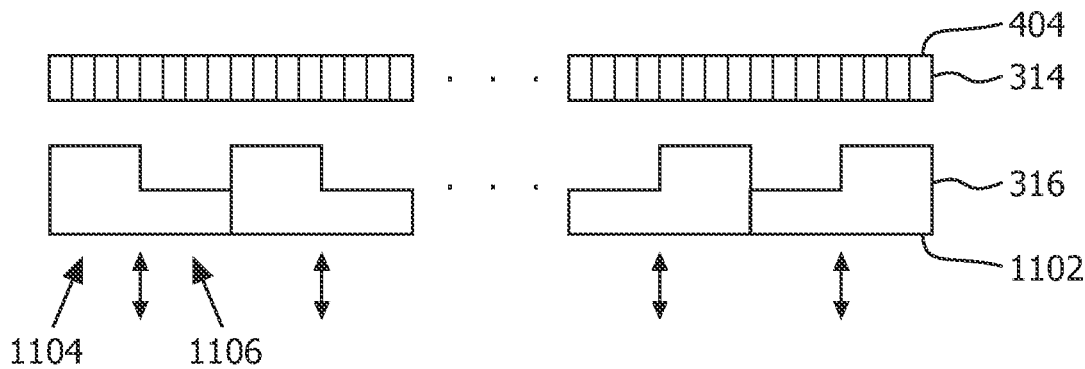
FIG. 11 illustrates an embodiment in which the dynamic post-patient filter includes a single row of stair case shaped filter segments.

FIG. 11 illustrates another non-limiting example of the filter 316. In this example, the filter 316 includes a single row of stair case filter segments 1102. With this embodiment, each row is configured to move between at least three positions, a first position in which the segments are not over the detector pixels (as shown), a second position in which a first portion 1104 of a filter segment 1102 covers detector pixels, and a third position in which the first portion and a second portion 1106 (or the entire filter segment 1102) covers detector pixels. In other embodiment, the stair case filter segments 1102 may include more than two steps (filter regions). Furthermore, the stair case filter segments 1102 can also be used in a two row interleaved manner similar to the embodiment of FIG. 10.

Relative to the embodiment of FIGS. 5-7, the embodiments of FIGS. 8-12 include less motors 318 as each filter segment covers more than a single detector pixel, which may reduce the amount of hardware (e.g., motors, encoders, etc.), the footprint for the hardware, and the cost of the hardware used to move the filter 316.

Figure 12:
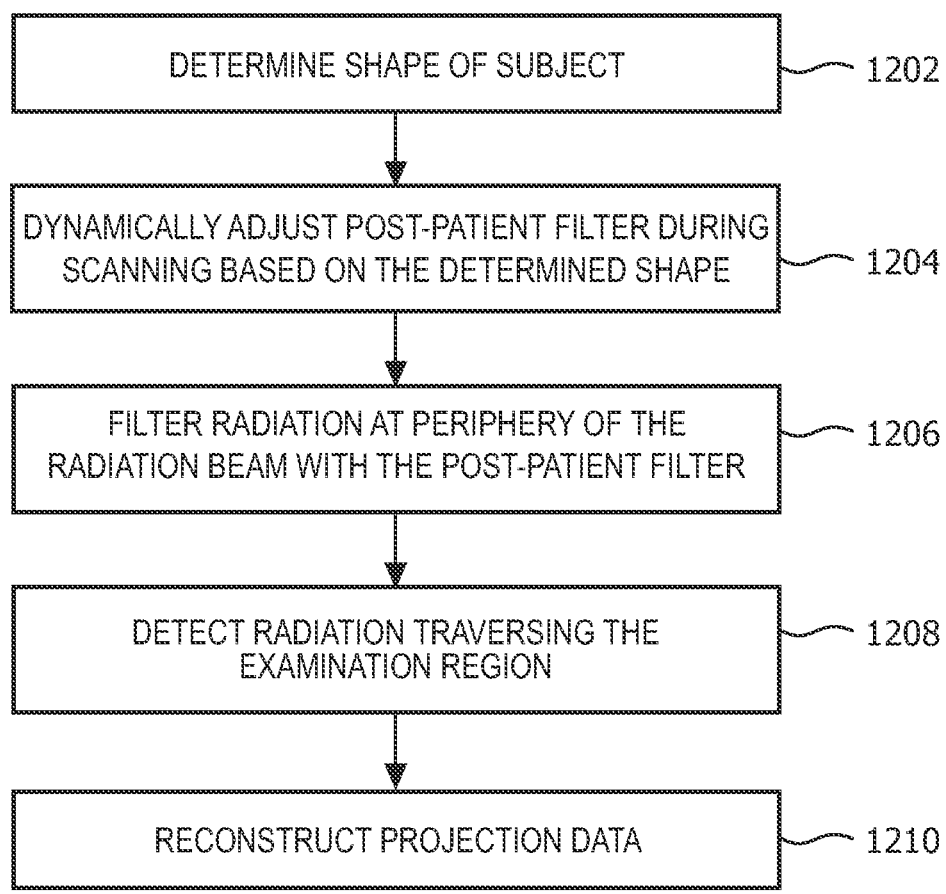
FIG. 12 illustrates an example method for reducing x-ray flux in peripheral regions of a radiation beam utilizing a dynamic post-patient filter in which the dynamic post-patient filter is dynamically adjusted to cover a sub-set of detectors of a detector array based on a shape of the subject being scanned.

FIG. 12 illustrates a method.

It is to be appreciated that the ordering of the acts is not limiting. As such, in other embodiments, the ordering of the acts may be different. In addition, one or more of the acts can be omitted and/or one or more other acts can be added.

At 1202, a shape of a subject (or object) being scanned is determined. As described herein, the shape can be determined via a pre-scan and/or during scanning.

At 1204, a dynamic post-patient filter is dynamically adjusted over the detector array during scanning the subject based on the determined shape.

At 1206, the dynamic post-patient filter filters radiation traversing regions at the periphery of the radiation beam from within and near the perimeter of the subject to the outer rays of the radiation beam.

At 1208, the filtered and unfiltered radiation traversing the examination region is detected and projection data indicative thereof is generated.

At 1210, the projection data is reconstructed, generating volumetric image data.

The above can be implemented by way of one or more processors executing one or more computer readable instructions encoded on computer readable storage medium such as physical memory. Additionally or alternatively, the computer readable instructions can be included in a signal or carrier wave.

It is to be appreciated that any shortcoming of reduced dose utilization is a minor effect since the filter 316 mainly attenuates non-attenuated x-rays and only a very small fraction of rays traversing a periphery of the patient.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. An imaging system, comprising:
    a radiation source configured to rotate around an examination region about a z-axis includes a focal spot that emits a radiation beam that traverses the examination region;
    a radiation sensitive detector array includes a plurality of detector pixels that detects radiation traversing the examination region and generates projection data indicative of the detected radiation; and a dynamic post-patient filter including one or more filter segments configured to selectively and dynamically move in front of the detector array between the detector array and the examination region and into and out of a path of the radiation beam illuminating the detector pixels during scanning an object or subject based on a shape of the object or subject, thereby filtering unattenuated radiation and radiation traversing a periphery of the object or subject.

2. The system of claim 1, further comprising:
at least one motor for moving the one or more filter segments; and
a controller that controls the motor to dynamically move the one or more filter segments into and out of the path of the radiation beam during scanning the object or subject.

3. The system of claim 2, the at least one motor, comprising:
a different sub-motor for controlling each of the one or more filter segments, wherein each filter segment corresponds to a different one of the detector pixels.

4. The system of claim 2, the at least one motor, comprising:
at least one sub-motor that controls a filter segment corresponding to more than one of the detector pixels.

5. The system of claim 1, wherein a different number of the one or more filter segments moves in front of the detector array and into the path of the radiation beam for different data acquisition intervals at different acquisition angles based on the shape of the object or subject.

6. The system of claim 1, wherein the one or more filter segments are configured to move in a direction of the z-axis, perpendicular to the path of the radiation beam.

7. The system of claim 1, wherein the one or more filter segments are configured to move in a direction transverse to the z-axis and perpendicular to the path of the radiation beam.

8. The system of claim 1, wherein the filter includes two rows of interleaved filter comb segments that alternately move into the path of the radiation beam, providing filtering for every other group of detector pixels.

9. The system of claim 8, wherein a detector reading corresponding to a partially covered detector pixel is replaced with a reading derived from adjacent neighboring uncovered detector pixels.

10. The system of claim 1, wherein at least one of the filter segments includes two different filter regions, each corresponding to a different number of detector pixels.

11. The system of claim 10, wherein one of the filter regions is moved in front of the detector pixels to filter radiation for a first set of detector pixels, and the other of the filter regions is moved in front of the detector pixels to filter radiation for a second set of detector pixels, which includes a greater number of detector pixels and the detector pixels of the first set.

12. The system of claim 1, wherein the radiation sensitive detector array includes at least one spectral detector.

13. The system of claim 1, wherein the one or more filter segments are asymmetrically moved with respect to a center of the detector array.

14. The system of claim 1, wherein the shape of the object or subject is determined based on a pre-scan of the object or subject or estimated during scanning based on relative intensity values of the detected radiation.

15. A method, comprising:
filtering peripheral rays of an emitted radiation beam traversing an examination region with dynamically adjustable filter segments configured to selectively move in and out of a region in front of a detector array and between the detector array and an examination region during scanning of an object or subject based on a shape of the object or subject, thereby filtering unattenuated radiation and radiation traversing a periphery of the object or subject.

16. The method of claim 15, wherein each segment corresponds to a single detector pixel of the detector array and individually moves in and out of the region in connection with the corresponding single detector pixel based on the shape of the object or subject.

17. The method of claim 15, wherein each segment corresponds to two or more detector pixels of the detector array and moves in and out of the region in connection with the corresponding two or more detector pixels.

18. The method of claim 15, wherein at least two of the segments alternately move in front of the detector array to provide filtering for every other group of detector pixels.

19. The method of claim 18, wherein the at least two of the segments are positioned on opposite sides of the detector array.

20. The method of claim 18, wherein detection readings for a group of detector pixels partially covered by one of the segments are replaced by detection readings interpolated from detection readings of adjacent uncovered groups of detector pixels.

21. The method of claim 15, wherein a segment includes a first region corresponding to a first number of detector pixels and a second region corresponding to a second greater number of detector pixels including the detector pixels in the first region, and at least one of the first or the second region is moved in front of the detector array to filter radiation.

22. The method of claim 15, further comprising:
determining the shape of the object or subject based on a pre-scan of the object or subject.

23. The method of claim 15, further comprising:
estimating the shape of the object or subject based on relative intensity values of the detected radiation.

24. A method for reducing a flux of peripheral rays of a radiation beam, comprising:
dynamically filtering the peripheral rays during scanning of an object or subject by selectively positioning physical filter segments of a dynamically adjustable post-patient filter between a detector array and an examination region of an imaging system based on a shape of the object or subject,
wherein the filter segments filter outer peripheral regions of the radiation beam, thereby reducing x-ray flux at the peripheral regions of the radiation beam.

* * * * *